(12) United States Patent
Schmidt et al.

(10) Patent No.: US 10,251,768 B2
(45) Date of Patent: Apr. 9, 2019

(54) INTRAGASTRIC BALLOON RETRIEVAL SYSTEMS AND RELATED METHODS

(71) Applicant: Boston Scientific Scimed, Inc., Maple Grove, MN (US)

(72) Inventors: Brian L. Schmidt, White Bear Lake, MN (US); James P. Rohl, Prescott, WI (US); Devon N. Arnholt, Shoreview, MN (US); Joel T. Eggert, Plymouth, MN (US); Mary M. Byron, Roseville, MN (US); Douglas D. Pagoria, Forest Lake, MN (US); Todd College, Little Canada, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1000 days.

(21) Appl. No.: 14/523,095

(22) Filed: Oct. 24, 2014

(65) Prior Publication Data
US 2015/0119921 A1    Apr. 30, 2015

Related U.S. Application Data

(60) Provisional application No. 61/896,947, filed on Oct. 29, 2013.

(51) Int. Cl.
*A61F 5/00* (2006.01)

(52) U.S. Cl.
CPC ............ *A61F 5/0089* (2013.01); *A61F 5/003* (2013.01); *A61F 5/0036* (2013.01)

(58) Field of Classification Search
CPC .... A61B 2017/00597; A61B 17/12022; A61B 17/12027; A61B 17/12031; A61B 17/12036; A61B 17/1204; A61B 17/221; A61F 5/0089; A61F 5/0036; A61F 5/0003; A61F 2/013; A61F 2/01; A61F 2/02; A61F 2/95; A61F 2002/011; A61F 2002/015; A61F 2002/016; A61F 2002/9505; A61F 2002/9522; A61F 2002/9528; A61F 2002/9534; A61M 2025/1054; A61M 2025/1065; A61M 2210/1053

(Continued)

(56) References Cited

U.S. PATENT DOCUMENTS

2007/0198074 A1\* 8/2007 Dann ............... A61B 17/00234
623/1.11
2007/0288033 A1  12/2007 Murature et al.
2010/0168783 A1\* 7/2010 Murature ......... A61B 17/22031
606/192

FOREIGN PATENT DOCUMENTS

WO    WO 2007/146822 A1    12/2007

\* cited by examiner

*Primary Examiner* — Todd J Scherbel
*Assistant Examiner* — Chima U Igboko
(74) *Attorney, Agent, or Firm* — Bookoff McAndrews, PLLC

(57) ABSTRACT

According to aspects of the present disclosure, a retrieval catheter assembly for retrieving an intragastric balloon may include a tubular member configured to pass through a wall of the intragastric balloon. The retrieval catheter assembly may also include a retrieval member coupled to the tubular member and movable between an undeployed configuration and a deployed configuration. In the undeployed configuration the retrieval member may be substantially aligned with the tubular member. In the deployed configuration at least a portion of the retrieval member may diverge from the tubular member and may be configured to engage the wall of the intragastric balloon.

7 Claims, 3 Drawing Sheets

(58) Field of Classification Search
USPC .................................. 606/113, 114, 127, 128
See application file for complete search history.

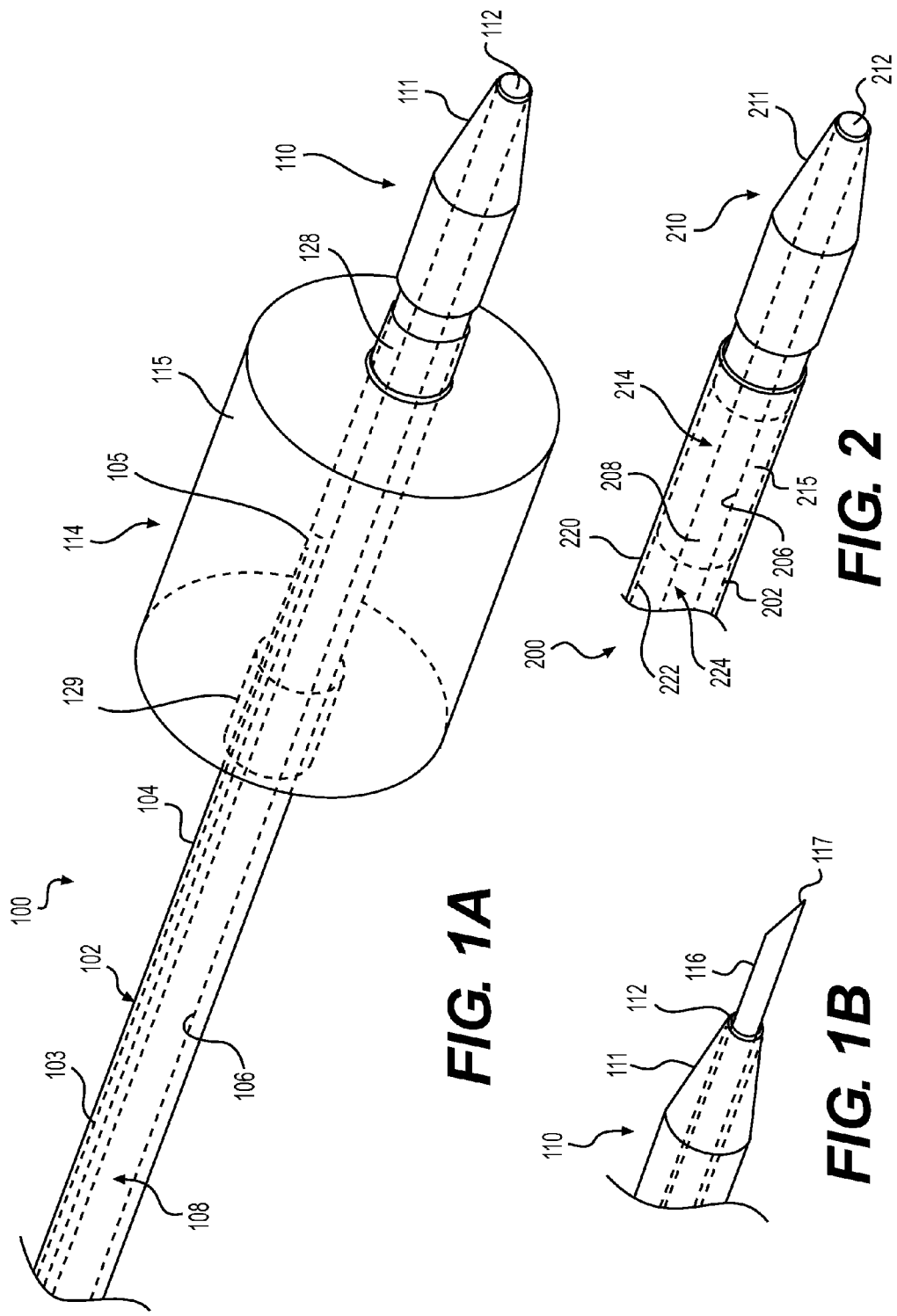

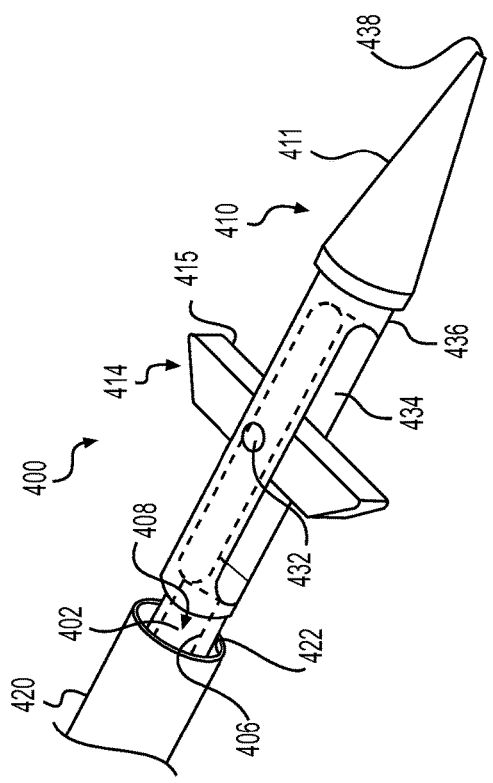
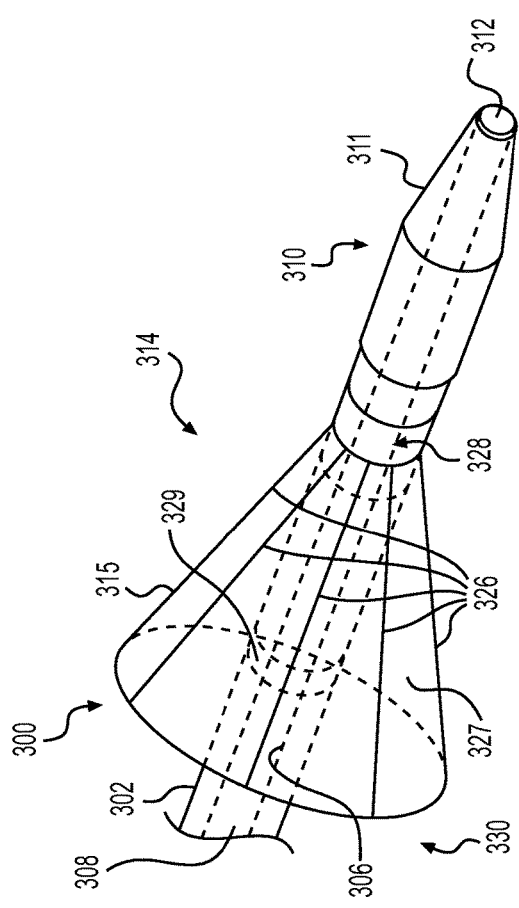
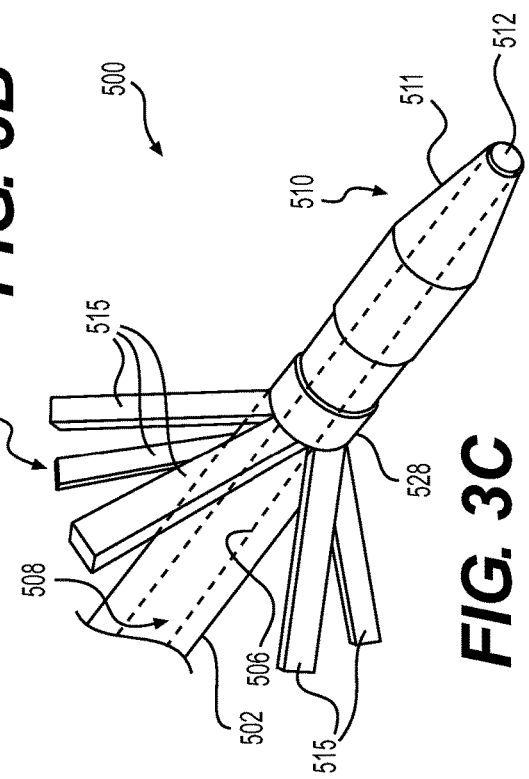

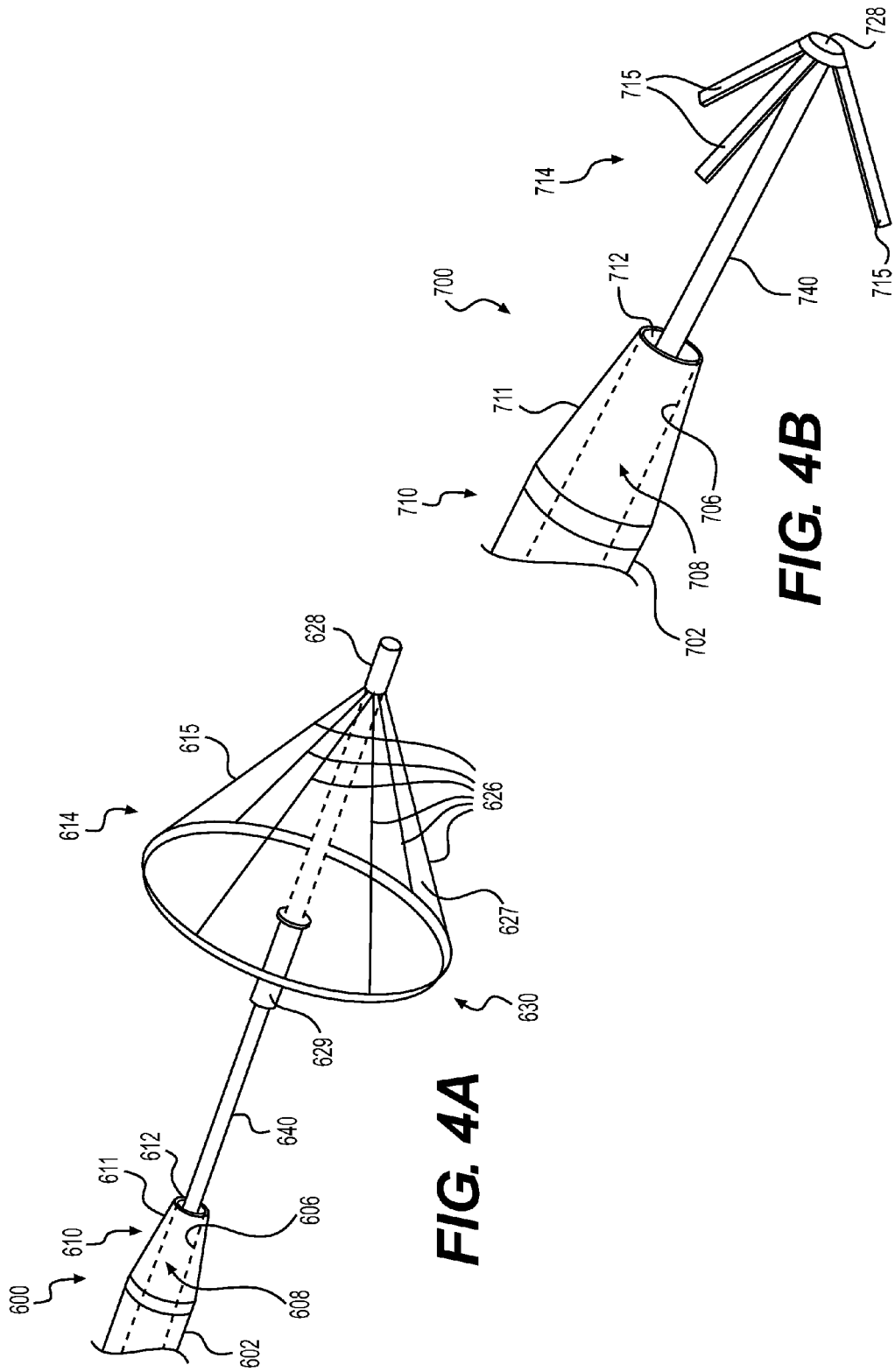

INTRAGASTRIC BALLOON RETRIEVAL SYSTEMS AND RELATED METHODS

CROSS-REFERENCE TO RELATED APPLICATIONS

This application claims the benefit of priority from U.S. Provisional Application No. 61/896,947, filed Oct. 29, 2013, which is incorporated by reference herein in its entirety.

TECHNICAL FIELD

The present disclosure generally relates to medical devices and methods, and in particular, medical devices and related methods for intragastric balloons.

BACKGROUND

An intragastric balloon is a device that may be inserted into a subject's stomach, and inflated, for obesity treatment. Such placement of intragastric balloons may be temporary, so intragastric balloons may be removed from the subject's stomach after a period of time.

Multiple medical devices may be used to perform steps for deflating and removing an inflated intragastric balloon from a subject's stomach. For example, a first medical device may be used to puncture the inflated intragastric balloon. Another medical device may be used to deflate the intragastric balloon. Yet another device may be used to grasp the deflated intragastric balloon for removing it from the subject's stomach. The use of multiple devices may be inefficient.

Some medical devices attempt to combine steps by using a single medical device to deflate the inflated intragastric balloon and grasp the deflated intragastric balloon. However, in some instances, the device, when grasping one or more portions of the intragastric balloon, may move the material forming the intragastric balloon in a way that obstructs the outflow of fluid from the intragastric balloon. This may make removing the intragastric balloon from the stomach more difficult, since a partially inflated intragastric balloon is larger, and more difficult to maneuver, than a deflated intragastric balloon. Further, some grasping devices may fail to adequately grasp or secure the intragastric balloon for withdrawing it from the subject's stomach.

In view of the above, there remains a need for devices and methods for deflating and removing intragastric balloons in a reliable and efficient manner.

SUMMARY OF THE DISCLOSURE

The disclosure is directed to medical devices and related methods for intragastric balloons. In some embodiments, the disclosure provides devices and methods for deflating an inflated intragastric balloon and removing the deflated intragastric balloon from a subject's stomach.

According to aspects of the present disclosure, a retrieval catheter assembly for retrieving an intragastric balloon may include a tubular member configured to pass through a wall of the intragastric balloon. The retrieval catheter assembly may also include a retrieval member coupled to the tubular member and movable between an undeployed configuration and a deployed configuration. In the undeployed configuration the retrieval member may be substantially aligned with the tubular member. In the deployed configuration at least a portion of the retrieval member may diverge from the tubular member and may be configured to engage the wall of the intragastric balloon According to aspects of the present disclosure, a method for retrieving an intragastric balloon including a wall with an interior surface may include inserting a tubular member, and a retrieval member mounted on the tubular member, through a recently created or planned opening in the wall of the intragastric balloon, with the retrieval member in an undeployed configuration. In the undeployed configuration the retrieval member may be substantially aligned with the tubular member. The method may also include deploying the retrieval member. In the deployed configuration at least a portion of the retrieval member may diverge from the tubular member. The method may also include exerting a pulling force on the tubular member in a proximal direction to engage the interior surface of the wall of the intragastric balloon with one or more engagement surfaces of the deployed retrieval member.

According to aspects of the present disclosure, a retrieval catheter assembly for retrieving an intragastric balloon may include a tubular member configured to pass through a wall of the intragastric balloon. The catheter assembly may also include a retrieval member operatively coupled to the tubular member. The retrieval member may have a plurality of arms, and may be movable between an unexpanded configuration and an expanded configuration. In the expanded configuration each arm of the plurality of arms may extend radially away from a longitudinal axis of the tubular member, with a proximal end of each arm being further from the longitudinal axis than a distal end of each arm. The proximal end of each arm may be configured to exert a force on an interior surface of the wall of the intragastric balloon when pulled into engagement with the wall of the intragastric balloon.

Additional characteristics, features, and advantages of the described embodiments will be set forth in part in the description that follows, and in part will be apparent from the description, or may be learned by practicing the disclosure. The disclosed subject matter can be realized and attained by way of the elements and combinations particularly pointed out in the appended claims.

It is to be understood that both the foregoing general description and the following detailed description are exemplary and explanatory only, and are not restrictive of the described embodiments, as claimed.

BRIEF DESCRIPTION OF THE DRAWINGS

The accompanying drawings, which are incorporated in, and constitute a part of this specification, illustrate exemplary embodiments of the present disclosure, and together with the description, serve to explain the principles of the disclosure.

FIG. 1A is a perspective view of a portion of a medical device, according to aspects of the present disclosure.

FIG. 1B is a perspective view of part of the medical device of FIG. 1A, according to aspects of the present disclosure.

FIG. 2 is a perspective view of a portion of another medical device, according to aspects of the present disclosure.

FIGS. 3A-3C are perspective views of portions of other medical devices, according to aspects of the present disclosure.

FIGS. 4A and 4B are perspective views of portions of other medical devices, according to aspects of the present disclosure.

DETAILED DESCRIPTION

Reference will now be made to embodiments of the present disclosure, examples of which are illustrated in the accompanying drawings. Wherever possible, the same reference numbers will be used throughout the drawings to refer to the same or like parts. The term "distal" refers to the end farthest away from a medical user when introducing a device in a subject. The term "proximal" refers to the end closest to the medical professional when placing a device in the subject.

Overview

Embodiments of this disclosure relate to systems for getting a catheter into an intragastric balloon through an entry port or opening in the intragastric balloon. Initially, the catheter may be inserted through a body lumen, and/or through a working channel of an endoscope, and maneuvered to the intragastric balloon. The entry port or opening in the intragastric balloon may be created by puncturing the intragastric balloon prior to inserting the catheter into the intragastric balloon. After inserting the catheter into the intragastric balloon, a locking mechanism or retrieval member coupled to the catheter may be deployed such that at least one of its dimensions may be greater than at least one dimension of the entry port or opening.

Exemplary Embodiments

FIG. 1A is a schematic view of a catheter assembly 100 configured to retrieve an inflated medical device, such as an inflated intragastric balloon (not shown). In general, an inflated intragastric balloon may be deployed in a subject's stomach cavity for weight-reduction therapy. After a period of time, the intragastric balloon may be deflated and removed from the subject's stomach using a device, such as the disclosed catheter assembly 100, as discussed below.

The catheter assembly 100 may include a tubular member 102. The tubular member 102 may have an outer surface 104, an inner surface 106 defining a central lumen 108, and a distal tip portion 110. The tubular member 102 may have a substantially cylindrical shape, with a substantially circular cross-section. Alternatively, other suitable cross-sectional shapes may also be used. Exemplary cross-sectional shapes may include rectangular, triangular, square, oblong, irregular, and/or any other shape or combination of shapes.

The central lumen 108 may extend along the longitudinal length of the tubular member 102. For example, the central lumen 108 may extend from a proximal end (not shown) of the tubular member 102 to a distal opening 112 at a distal end of the distal tip portion 110.

The tubular member 102 may be formed of any suitable material, including but not limited to, metals, metal alloys, polymers, and composite materials. The material may be substantially rigid, such that the tubular member 102 may retain its shape during use. Alternatively, the material may be substantially flexible, or at least semi-rigid, allowing bending or twisting of the tubular member 102, to help navigate the tubular member 102 through an opening or passage on its way to a subject's stomach, while still being rigid enough to penetrate an intragastric balloon. In some embodiments, the tubular member 102 may be coated with a lubricious material, such as a polytetrafluoroethylene (PTFE) like TEFLON, polyvinylchloride, high-density polyethylene (HDPE), or the like, that may reduce friction between the outer surface 104 of the tubular member 102 and surfaces that may come into contact with the outer surface 104.

The distal tip portion 110 of the tubular member 102 may include a cone-shaped member 111. The cone-shaped member 111 may have a larger diameter at its proximal end than at its distal end. The cone-shaped member 111 may possess a tapered configuration, which may facilitate insertion of the tubular member 102 through the subject's body, and through an opening in the intragastric balloon. The distal end of the cone-shaped member 111 may include the distal opening 112.

The catheter assembly 100 may also include a retrieval member 114. The retrieval member 114 may be fixedly coupled to the tubular member 102 such that the retrieval member 114 may not slide relative to the tubular member 102 when in use. The retrieval member 114 may extend circumferentially around the outer surface 104 of the tubular member 102, at or adjacent a proximal side of the distal tip portion 110.

The retrieval member 114 may move between deployed and undeployed configurations. In one embodiment, the retrieval member 114 may include an inflatable balloon 115. The deployed configuration (e.g., inflated or otherwise expanded) of the balloon 115 is shown in FIG. 1A. In the deployed configuration, the balloon 115 may diverge from the tubular member 102. For example, the balloon 115 may extend radially away from the outer surface 104 of the tubular member 102. The diameter of the inflated balloon 115 may be greater than the diameter of the opening in the intragastric balloon through which the deflated balloon 115 was inserted.

In contrast, in the undeployed configuration (e.g., deflated or otherwise unexpanded), the balloon 115 may be compressed against the tubular member 102. As such, the balloon 115 may be substantially aligned with the tubular member 102. For example, the balloon 115 may lie adjacent to, and/or substantially flush with, the outer surface 104 of the tubular member 102. In the undeployed configuration, an interior surface of the balloon 115 may contact the outer surface of the tubular member 102. With the retrieval member 114 in the undeployed configuration, its reduced profile may make it easier to maneuver the catheter assembly 100 through a body lumen and/or a working channel of an endoscope. The balloon 115 may be formed of any suitable material, including, for example, a polyether block amide like PEBAX, silicone, polyurethane, and/or an elastomer. It is also contemplated that the balloon 115 may be substantially elastic so that it may stretch as it is inflated, and may return to its unstretched form when deflated. It is also contemplated that the balloon 115 may include one or more folds when in the undeployed configuration, and the one or more folds may unfold as the balloon 115 moves to its deployed configuration.

The balloon 115 may include a proximal base 129 and a distal base 128, which may be sleeve-like members configured to secure the balloon 115 to the tubular member 102, and provide sealing engagement between the balloon 115 and the tubular member 102 to prevent undesired escape of the inflation fluid.

The balloon 115 may be inflated by directing an inflation fluid, such as air, saline, or any other suitable fluid into the balloon 115, through an inflation/deflation lumen 103 in a wall of the tubular member 102. The balloon 115 may be deflated by directing the fluid away from the balloon 115 through the lumen 103. It is contemplated that a proximal end (not shown) of the lumen 103 may be coupled to a pump and/or vacuum source to supply and/or withdraw the fluid from the balloon 115, and a distal end of the lumen 103 may terminate at an opening 105 in fluid communication with the interior of the balloon 115.

The catheter assembly 100 may be configured to receive a puncturing member 116, which may include a needle, as shown in FIG. 1B. The needle 116 may be guided distally through the central lumen 108 until it extends distally through the distal end opening 112 of the tubular member 102. The needle 116, when extended, may puncture the inflated intragastric balloon, thus creating a port or opening in the intragastric balloon. The tubular member 102 may enter the intragastric balloon via the opening. The needle 116 may include a sharp tip 117 to facilitate puncturing.

Although not shown, the needle 116 may be operably coupled to an actuation mechanism configured to push and/or pull the needle 116 as required. It is also contemplated that the needle 116 may be retracted into and/or withdrawn from the central lumen 108 of the tubular member 102 after being used to create the port or opening.

FIG. 2 shows another exemplary retrieval catheter assembly 200 for deflating and removing an inflated intragastric balloon from a subject's stomach. The catheter assembly 200 may include a tubular member 202. The tubular member 202 may include an inner surface 206 defining a central lumen 208. The tubular member 202 may also include a distal tip portion 210, with a cone-shaped member 211 and a distal opening 212.

The catheter assembly 200 may also include a retrieval member 214. The retrieval member 214 may be fixedly coupled to the tubular member 202. The retrieval member 214 may extend circumferentially around the tubular member 202. The retrieval member 214 may expand move from an undeployed configuration (FIG. 2), to a deployed configuration. The retrieval member 214 may move to its deployed or expanded configuration without requiring the use of an inflation fluid to inflate the retrieval member 214. Rather, the retrieval member 214 may be self-expanding. For example, the retrieval member 214 may include a self-expanding stent 215.

The self-expanding stent 215 may be formed by a self-expanding support structure covered by a sheath or membrane. The sheath or membrane may be coupled to the tubular member 202 by adhesives or any other suitable mechanical coupling at the ends of the sheath or membrane, and may limit relative motion between the deployed self-expanding support structure and the tubular member 202. The self-expanding stent 215 may include, for example, a self-expanding support structure made of a shape-memory material like Nitinol. Any other suitable material, or combination of materials, may also be used. Examples of constructions for self-expanding stent 215, and in particular the self-expanding support structure, are described in U.S. Pat. No. 5,665,115, U.S. Pat. No. 6,945,993, and U.S. Pat. No. 7,033,385, the disclosures of which are incorporated herein by reference in their entirety. The membrane may be made of silicone, polyurethane, an elastomer, and/or any other suitable material.

When the self-expanding stent 215 is in its undeployed configuration, interior surfaces of the self-expanding support structure and/or the sheath/membrane may be adjacent to or in contact with the outer surface of the tubular member 202. When the self-expanding stent 215 is in its deployed configuration, the self-expanding support structure and the sheath/membrane may diverge from the tubular member 202. For example, the self-expanding support structure and the sheath/membrane may move radially outward from the outer surface of the tubular member 202. The deployed self-expanding stent 215 may have a cylindrical shape similar to the cylindrical shape of the inflated balloon 115 (FIG. 1A). It is contemplated that the membrane may stretch as the self-expanding stent 215 moves to the deployed configuration. Additionally or alternatively, the membrane may include one or more pleats or folds when in the undeployed configuration. The membrane may be movable relative to the self-expanding support structure, allowing the one or more pleats or folds to unfold as the self-expanding support structure expands.

The self-expanding stent 215 may be held in its undeployed configuration by an outer sheath 220. The outer sheath 220 may include an inner surface 222 defining a central lumen 224. The central lumen 224 may receiving the tubular member 202 and the self-expanding stent 215. The distal end portion 210 may remain outside of the outer sheath 220, at a distal end of the outer sheath 220, while the rest of the tubular member 202 is within the central lumen 224 of the outer sheath 220. When the self-expanding stent 215 is within the central lumen 224, the inner surface 222 of the outer sheath 220 may prevent the self-expanding stent 214 from deploying. Prior to deployment, the self-expanding stent 215 may be compressed against the outer surface of the tubular member 202. The self-expanding stent 215 may be contained within the outer sheath 220 during insertion of the catheter assembly 200 into the subject's stomach, and during insertion of the catheter assembly 200 through the opening in a wall of an inflated intragastric balloon. The opening may be created using, for example, the puncturing member 116, by extending the puncturing member 116 out of the distal end opening 212.

The tubular member 202 and the self-expanding stent 215 may be extended distally relative to the outer sheath 220, and/or the outer sheath 220 may be retracted proximally relative to the tubular member 202 and the self-expanding stent 215, to extend the tubular member 202 and the self-expanding stent 215 out from within the central lumen 224 of the outer sheath 220. The self-expanding stent 215 may expand to its deployed configuration upon emerging from the outer sheath 220, at the urging of the self-expanding support structure. In the deployed configuration, the self-expanding stent 215 may extend radially away from the outer surface of the tubular member 202. Once deployed, the self-expanding stent 215 may be wider than the opening in the wall of the intragastric balloon, and thus, the self-expanding stent 215 may engage the wall of the intragastric balloon when the tubular member 202 and the self-expanding stent 215 are pulled in a proximal direction.

The outer sheath 220 may be manufactured from any suitable material, which may be biocompatible, including but not limited to, metals, metal alloys, polymers, and composite materials. The material may be substantially rigid, such that the outer sheath 220 may retain its shape during use. Alternatively, the material may be substantially flexible, allowing bending or twisting of the outer sheath 220, to help navigate the outer sheath 220 through an opening, passage, or working channel of an endoscope, on its way to a subject's stomach, while still being rigid enough to penetrate an intragastric balloon if desired. In some embodiments, the outer sheath 220 may be coated with a lubricious material, such as a PTFE like TEFLON, polyvinylchloride, HDPE, or the like, that may reduce friction between the outer surface of the outer sheath 220 and surfaces that may come into contact with the outer surface.

FIGS. 3A-3C show other exemplary retrieval catheter assemblies. The retrieval catheter assembly 300, shown in FIG. 3A, may include a tubular member 302 with a central lumen 308 defined by an inner surface 306. The central lumen 308 may terminate at a distal end opening 312. The tubular member 302 may also include a distal end portion 310 including a cone-shaped member 311 and the distal end opening 312.

The catheter assembly 300 may also include a retrieval member 314. The retrieval member 314 may include a self-expanding member 315. The self-expanding member 315 may be fixedly coupled to the tubular member 302, and may extend circumferentially around the tubular member 302. The self-expanding member 315 may include a plurality of arms 326. The arms 326 may be pre-bent at or near their proximal ends. In the absence of a restraining force that keeps the arms 326 straight, the arms 326 may move to their bent state. The arms 326 may support a sheath or sheath panels 327. The self-expanding member 315 may move from an undeployed configuration (e.g., unexpanded) to a deployed configuration (e.g., expanded) when the arms 326 return to their bent state.

The retrieval member 314 may be coupled to the tubular member 302. For example, although not required, the self-expanding member 315 may be mounted to the tubular member 302 by a proximal base 329 and a distal base 328. At least one of the proximal base 329 and the distal base 328 may be adhesively coupled to the tubular member 302, or coupled by any other suitable mechanical coupling. Distal ends of the arms 326 may be coupled to the distal base 328. Proximal ends of the arms 326 may move relative to the proximal base 329, while being coupled to the proximal base 329 by a proximal facing end of the sheath 327. Alternatively, the distal ends of the arms 326 may be directly coupled to the tubular member 302 without requiring proximal or distal bases.

The self-expanding member 315 may be held in its undeployed configuration by being received in a central lumen defined by an inner surface of an outer sheath (not shown) surrounding the tubular member 302 and the retrieval member 314, similar to the outer sheath 220. The distal end portion 310 may remain outside of the outer sheath, at a distal end of the outer sheath, while the rest of the tubular member 302 is within the outer sheath. When the self-expanding member 315 is in the unexpanded configuration, the arms 326 and the sheath 327 may be compressed against the outer surface of the tubular member 302. For example, the arms 326 and the sheath 327 may be in contact with, and substantially parallel to, the outer surface of the tubular member 302. The arms 326 may be made of any suitable material including, for example, a shape-memory material like Nitinol. The sheath 327 may be made of any suitable material including, for example, PEBAX, silicone, polyurethane, and/or an elastomer. The sheath 327 may be elastic, and may stretch as the self-expanding member 315 moves to its deployed configuration. Additionally or alternatively, the sheath 327 may include one or more folds that may unfold as the self-expanding member 315 moves to its deployed configuration.

The self-expanding member 315 may move from its undeployed configuration to its deployed configuration by extending the tubular member 302 and the self-expanding member 315 out of the outer sheath. When the self-expanding member 315 is free from the outer sheath, the arms 326 may move toward their bent state, diverging from the tubular member 302. For example, the arms 326 may extend radially away from the outer surface of the tubular member 302 (FIG. 3A). When free of the outer sheath, the arms may form an angle with the outer surface of the tubular member 302 and the longitudinal axis of the tubular member 302. The arms 326 in the deployed configuration may form any suitable angle with respect to the outer surface and the longitudinal axis of the tubular member 302, including, for example, an acute angle or a right angle. The diameter of the self-expanding member 315, when in the deployed state, may be larger than the diameter of the opening in the intragastric balloon through which the undeployed self-expanding member 315 was inserted.

A retrieval catheter assembly 400 is shown in FIG. 3B. The catheter assembly 400 may include a tubular member 402 with a central lumen 408 defined by an inner surface 406. The tubular member 402 may also include a distal tip portion 410. The distal tip portion 410 may include a conical member 411 terminating at a distal end tip 438. The distal end tip 438 may be configured to puncture tissue and/or a wall of an intragastric balloon. Thus, the catheter assembly 400 may be considered needleless, in that a needle 116 is not required when the catheter assembly 400 is used to deflate and retrieve an intragastric balloon.

The distal tip portion 410 may also include a proximal housing 436. The proximal housing 436 may include a slot 434 extending from a first end of the proximal housing 436 to a second end of the proximal housing 436, the second end being opposite the first end.

The slot 434 may receive a retrieval member 414. The retrieval member 414 may include a bar 415. The bar 415 may be rotatably coupled to the proximal housing 436 by a pin 432. The pin 432 may extend across the slot 434 from a first side of the slot 434 to a second slide of the slot opposite the first side. The bar 415 may include an elongated structure having a substantially trapezoidal shape. Alternatively, the bar 415 may have a rectangular, cylindrical, triangular, polygonal, or irregular shape. The dimensions of the slot 434 may be selected to accommodate the bar 415. The bar 415, pin 432, and proximal housing 436 may be formed from a suitable material, such as metals, metal alloys, or polymers.

In the undeployed configuration, the longitudinal axis of the bar 415 may be parallel to or aligned with the longitudinal axis of the proximal housing 436, such that the bar 415 can pass through the outer sheath 420. The bar 415 may be retained in the undeployed configuration by an inner surface 422 of an outer sheath 420 when the bar 415 is received within the outer sheath 420. The distal end portion 410 may remain outside of the outer sheath 420, near the distal end of the outer sheath 420, while the rest of the tubular member 402 is within the outer sheath 420.

Once the outer sheath 420 is retracted distally and/or the bar 415 is extended proximally, the bar 415 may exit from the distal end of the outer sheath 420 and rotate to its deployed configuration. In the deployed configuration, opposite ends of the bar 415 may diverge from the tubular member 402. For example, opposite ends of the bar 415 may protrude from the slot 434. The longitudinal axis of the bar 415 may be substantially perpendicular to the longitudinal axis of the proximal housing 436 (FIG. 3B). The bar 415 may be biased toward the deployed configuration by a spring (not shown) or similar biasing device. Once in the deployed configuration, the width of the bar 415 may be larger than the diameter of the opening in the intragastric balloon through which the undeployed bar 415 was inserted.

The central lumen 408 of the tubular member 402 may be in fluid communication with the slot 434. For example, a distal end opening of the central lumen 408 may be located at a surface of the proximal housing 436 forming the slot 434. Fluid in an inflated intragastric balloon may travel into the slot 434, and then into the central lumen 408, to deflate the intragastric balloon. It is also contemplated that fluid may be removed from the intragastric balloon via the lumen defined by the inner surface 422 of the outer sheath 402.

The retrieval catheter assembly 500, shown in FIG. 3C, may include a tubular member 502 with a central lumen 508 defined by an inner surface 506. The central lumen 508 may terminate at a distal end opening 512. The tubular member 502 may also include a distal end portion 510 including a cone-shaped member 511 and the distal end opening 512.

The catheter assembly 500 may also include a retrieval member 514. The retrieval member 514 may include a plurality of prongs or arms 515. The arms 515 may be fixedly coupled to the tubular member 502, and may extend circumferentially around the tubular member 502. The arms 515 may be coupled to a distal base 528, with the base 528 being coupled to the tubular member 502 by an adhesive or any other suitable mechanical coupling. Alternatively, distal ends of the arms 515 may be directly mounted on the tubular member 502 without requiring use of the base 528. The arms 515 may move from an undeployed configuration (e.g., unexpanded) to a deployed configuration (e.g., expanded) (FIG. 3C). The arms 515 and the distal base 428 may be pre-bent such that the arms 515 may diverge from the tubular member 502 by extending radially outwardly in the absence of a restraining force.

The arms 515 may be held in their undeployed configurations by an inner surface of an outer sheath (not shown) similar to the inner surface 222 and outer sheath 220. It is contemplated that the distal end portion 510 may remain outside of the outer sheath, near a distal end of the outer sheath, while the rest of the tubular member 502 is within the outer sheath. When the arms 515 are in the undeployed configuration, the arms 515 may be compressed against the outer surface of the tubular member 502. For example, the arms 515 may be in contact with, and substantially parallel to, the inner surface of the sheath and/or the outer surface of the tubular member 502. The arms 515 may be made of any suitable material including, for example, a shape-memory material like Nitinol.

The arms 515 may move from their undeployed configurations to their deployed configurations by extending the tubular member 502 and the arms 515 out of the outer sheath. When the arms 515 are free from the outer sheath, the arms 515 may extend radially away from the tubular member 502 to their bent state, thus forming an angle with the outer surface and the longitudinal axis of the tubular member 502. The arms 515 in the deployed configuration may form any suitable angle with respect to the outer surface and the longitudinal axis of the tubular member 502, including, for example, an acute angle or a right angle. Once expanded, the diameter of the retrieval member 514, and/or the distance between the arms 515, may be larger than the diameter of the opening in the intragastric balloon through which the undeployed retrieval member 514 was inserted.

FIG. 4A shows a catheter assembly 600 including a tubular member 602, with a central lumen 608 defined by an inner surface 606 of the tubular member 602. The central lumen 608 may terminate at a distal end opening 612. The tubular member 602 may also include a distal end portion 610 including a cone-shaped member 611 and the distal end opening 612.

The retrieval member 614 may include a self-expanding member 615 coupled to a shaft 640. The self-expanding member 615 may extend circumferentially around the shaft 640. The self-expanding member 615 may include a plurality of arms 626. The arms 626 may support a sheath or sheath panels 627. Distal ends of the arms 626 may be fixedly coupled to the shaft 640, while proximal ends of the arms 626 may be movable relative to the shaft 640. For example, the distal ends of the arms 626 may be coupled to a distal base 628 that is coupled to the shaft 640 by an adhesive or any other suitable mechanical coupling. Alternatively, the distal ends of the arms 626 may be directly mounted to the shaft 640 by any suitable mechanical coupling. Longitudinally extending portions of the sheath/panels 627 may be coupled to the arms 626 by an adhesive or any other suitable mechanical coupling. Additionally or alternatively, a distal end portion of the sheath/panels 627 may be coupled to the proximal ends of the arms 626. The proximal base 629 may be coupled to the shaft 640 by any suitable coupling, including adhesive. Alternatively, the proximal base 629 may be slidably coupled to the shaft 640. The self-expanding member 615 may move from an undeployed configuration (e.g., unexpanded) to a deployed configuration (e.g., expanded), in the absence of a restraining force keeping the self-expanding member 615 in the undeployed configuration.

The self-expanding member 615 may be held in its undeployed configuration when received in the central lumen 608. The inner surface 606 of the tubular member 602 may exert the restraining force on the self-expanding member 615.

When the self-expanding member 615 is in the undeployed configuration, the arms 626 and the sheath 627 may be compressed against the outer surface of the shaft 640. For example, the arms 626 and the sheath 627 may be in contact with, and substantially parallel to, the outer surface of the shaft 640 and/or the inner surface 606. The arms 626 may be made of any suitable material including, for example, a shape-memory material like Nitinol. The sheath 627 may be made of any suitable material including, for example, PEBAX, silicone, polyurethane, and/or an elastomer. The sheath 627 may be elastic, and may stretch as the self-expanding member 615 moves to its deployed configuration. Additionally or alternatively, the sheath 627 may include one or more folds that may unfold as the self-expanding member 615 moves to its deployed configuration.

The self-expanding member 615 may move from its undeployed configuration to its deployed configuration by extending the shaft 640 and the self-expanding member 615 out of the central lumen 608. When the self-expanding member 615 is free from the central lumen 608, the arms 626 may diverge from the shaft 640. For example, the arms 626 may extend radially away from the shaft 640, thus forming an angle with the outer surface of the shaft 640, and/or the longitudinal axis of the tubular member 602. The arms 626 in the deployed configuration may form any suitable angle with respect to the outer surface of the shaft 640 and/or the longitudinal axis of the tubular member 602, including, for example, an acute angle or a right angle. The self-expanding member 615 may have a tapering conical shape. Once in the deployed configuration, the self-expanding member 615 may have a diameter at its proximal end that is larger than a diameter of the opening through which the tubular member 602 was inserted.

FIG. 4B shows another deflation and retrieval catheter assembly 700. The catheter assembly 700 may include a tubular member 702 with a central lumen 708 defined by an inner surface 706. The central lumen 708 may terminate at a distal end opening 712. The tubular member 702 may also include a distal end portion 710 including a cone-shaped member 711 and the distal end opening 712.

The retrieval member 714 may include prongs or arms 715, fixedly coupled to a shaft 740. The arms 715 may be positioned circumferentially around the shaft 740. The arms 715 may move from an undeployed configuration (e.g., unexpanded) to a deployed configuration (e.g., expanded), and may be pre-bent or otherwise biased toward the deployed configuration. Distal ends of the arms 715 may be coupled to a distal base 728, which may be coupled to the tubular member 702 by an adhesive or any other suitable mechanical coupling. Alternatively, the distal ends of the arms 715 may be directly mounted on the tubular member 702 by adhesive or any other suitable mechanical coupling.

The arms 715 may be held in their undeployed configurations by the inner surface 706 of the tubular member 702, when the prongs 715 are received in the central lumen 708 of the tubular member 702. When the arms 715 are in the undeployed configuration, they may be compressed against the outer surface of the shaft 740. For example, the arms 715 may be in contact with, and substantially parallel to, the outer surface of the shaft 740 and/or the inner surface 706. The arms 715 may be made of any suitable material including, for example, a shape-memory material like Nitinol.

The arms 715 may move from their undeployed configuration to their deployed configuration, by extending the shaft 740 and the arms 715 out of the central lumen 708. When the arms 715 are free from the central lumen 708, the arms 715 may diverge from the shaft 740. For example, the arms 715 may extend radially away from the shaft 740, thus forming an angle with the outer surface of the shaft 740 and/or the longitudinal axis of the tubular member 702. The arms 715 in their deployed configuration may form any suitable angle with respect to the outer surface of the shaft 740 and/or the longitudinal axis of the tubular member 702, including, for example, an acute angle or a right angle. Once deployed, the diameter of the retrieval member 714, and/or the space between arms 715, may be larger than the diameter of the opening in the intragastric balloon through which the tubular member 702 was inserted.

Exemplary steps for retrieving an inflated gastric balloon from a subject's stomach will now be described. The first step may include inserting a retrieval catheter assembly, such as any of the retrieval catheter assemblies 100, 200, 300, 400, 500, 600, or 700, into the subject. The catheter assembly may be inserted through an anatomical opening, such as a subject's mouth. Alternatively, the catheter assembly may be inserted through a working channel of an endoscope. For the catheter assemblies 200, 300, 400, and 500, the catheter assembly may be at least partially received within the outer sheath during insertion. For the catheter assemblies 600 and 700, the retrieval member may be received within the tubular member during insertion.

The next step may include navigating the catheter assembly to the stomach. If inserted through the subject's mouth, the catheter assembly may be navigated to the stomach through the subject's esophagus, or through the working channel of an endoscope inserted into the subject's esophagus. For the catheter assemblies 200, 300, 400, and 500, the catheter assembly may remain within its outer sheath during the navigation step. For the catheter assemblies 600 and 700, the retrieval member may remain within the tubular member during the navigation step.

A distal end of a tubular member of the catheter assembly may be positioned adjacent to and/or brought into contact with a surface of the inflated intragastric balloon. For the catheter assemblies 100, 200, 300, 500, 600, or 700, a puncturing member, similar to the needle 116, may be inserted into the central lumen of the tubular member, and moved distally to extend out of the distal end opening of the tubular member. The extended puncturing member may puncture the inflated intragastric balloon, creating an opening therein. For the catheter assembly 400, the tip of the distal end portion of the tubular member may puncture the inflated intragastric balloon, without requiring use of a needle.

If a needle is used to make the opening, the needle with be withdrawn from the tubular member after the opening has been made. The catheter assembly may be inserted into the interior of the intragastric balloon through the opening. The catheter assembly may be inserted far enough into the interior of the intragastric balloon to ensure that the retrieval member (in its unexpanded configuration) passes through the opening and into the balloon interior. The retrieval member may remain in its undeployed configuration during the above-described steps. For the catheter assemblies 200, 300, 400, and 500, the outer sheath may also be inserted into the interior of the intragastric balloon through the opening. For the catheter assemblies 600 and 700, after withdrawal of the needle, the retrieval member may be inserted into the tubular member.

The retrieval member may then move to its deployed configuration. When the retrieval member is in its deployed configuration, its proximal width may be larger than a width of the opening in the intragastric balloon through which the undeployed retrieval member was inserted. For the catheter assembly 100, the retrieval member may move to its deployed configuration by being inflated. For the catheter assemblies 200, 300, 400, and 500, the retrieval member may move to its deployed configuration by retracting the outer sheath in the proximal direction, and/or extending the tubular member and retrieval member in the distal direction. For the catheter assemblies 600 and 700, the retrieval member may move to its deployed configuration by retracting the tubular member in the proximal direction, and/or extending the retrieval member in the distal direction.

The intragastric balloon may be deflated. For the catheter assemblies 100, 200, 300, 500, 600, and 700, deflating the intragastric balloon may include directing fluid in the intragastric balloon through the distal end opening of the tubular member, into the central lumen of the tubular member, and out of the intragastric balloon. For the catheter assembly 400, deflating the intragastric balloon may include directing fluid therein through the openings of the slot, into the central lumen of the tubular member, and out of the intragastric balloon. It should be understood that the retrieval member may move to its expanded configuration before deflation, during deflation, or after deflation of the intragastric balloon.

Once the intragastric balloon has been deflated, and the retrieval member has moved to its deployed configuration, the retrieval member may be brought into contact with the interior surface of the intragastric balloon. For the catheter assemblies 100, 200, 300, 400, and 500, the tubular member, and thus, the retrieval member fixedly mounted thereon, may be moved proximally until the proximal end portions of the retrieval member engage the portion of the interior surface of the intragastric balloon surrounding the opening into the intragastric balloon. For the catheter assemblies 600 and 700, the tubular member and/or the retrieval member extending therefrom, may be moved proximally until the proximal end portions of the retrieval member engage the portion of the interior surface of the intragastric balloon surrounding the opening into the intragastric balloon. For the catheter assemblies 600 and 700, the portion of the inner surface of the intragastric balloon may even be clamped between the retrieval member and the distal end of the distal tip portion. The engagement between the intragastric balloon and the retrieval member may lock or link the deflated intragastric balloon to the retrieval member, allowing the retrieval member to be used to pull the intragastric balloon out of the stomach. For the catheter assembly 100, it is contemplated that the retrieval member 114 may be partially deflated to reduce its diameter, making it easier to remove from the subject's body, while still remaining sufficiently inflated to avoid being separated from the intragastric balloon.

Embodiments of the present disclosure may be applicable to various and different medical or non-medical procedures. In addition, certain aspects of the aforementioned embodiments may be selectively used in collaboration, or removed, during practice, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A method for retrieving an intragastric balloon including a wall with an interior surface, the method comprising:
    inserting a tubular member having a distal tip, and a retrieval member mounted on the tubular member, through an opening in the wall of the intragastric balloon, with the retrieval member in an undeployed configuration, wherein in the undeployed configuration the retrieval member is substantially aligned with the tubular member, wherein the retrieval member includes a plurality of prongs and a sheath supported by the plurality of prongs;
    deploying the retrieval member, wherein deploying the retrieval member includes expanding the sheath with the plurality of prongs and allowing the plurality of prongs to move radially outward from the tubular member, wherein in the deployed configuration at least a portion of the retrieval member diverges from the tubular member, and wherein in the deployed configuration the distal tip of the tubular member is disposed distally of an entirety of the retrieval member; and
    exerting a pulling force on the tubular member in a proximal direction to directly engage the interior surface of the wall of the intragastric balloon with one or more engagement surfaces of the deployed retrieval member.

2. The method of claim 1, further including creating the opening in the wall of the intragastric balloon by puncturing the intragastric balloon with a needle extended from a distal end opening of the distal tip of the tubular member.

3. The method of claim 1, wherein the tubular member includes a central lumen, the distal tip of the tubular member including a distal end opening in fluid communication with the central lumen.

4. The method of claim 3, wherein the retrieval member is mounted on an external surface of the tubular member.

5. The method of claim 1, wherein the retrieval member is coupled to a distal base.

6. The method of claim 5, wherein distal portions of the plurality of prongs are coupled to the distal base, and wherein the distal base is mounted on the tubular member.

7. The method of claim 5, wherein the retrieval member is coupled to a proximal base.

* * * * *